(12) United States Patent
Pacetti et al.

(10) Patent No.: US 7,220,816 B2
(45) Date of Patent: May 22, 2007

(54) BIOLOGICALLY ABSORBABLE COATINGS FOR IMPLANTABLE DEVICES BASED ON POLY(ESTER AMIDES) AND METHODS FOR FABRICATING THE SAME

(75) Inventors: Stephen D. Pacetti, San Jose, CA (US); Jessica R. DesNoyer, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 141 days.

(21) Appl. No.: 10/738,704

(22) Filed: Dec. 16, 2003

(65) Prior Publication Data

US 2005/0131201 A1 Jun. 16, 2005

(51) Int. Cl.
*C08G 63/02* (2006.01)

(52) U.S. Cl. .................. 528/272; 424/423; 427/207.1; 427/322; 428/478.2; 428/474.4; 528/289; 528/290; 528/291; 528/292; 528/335

(58) Field of Classification Search .............. 427/2.25, 427/2.28, 207.1, 322; 623/1.15, 1.46, 1.49; 428/423.1, 474.4, 478.2; 528/289, 290, 291, 528/292, 335; 424/423
See application file for complete search history.

(56) References Cited

U.S. PATENT DOCUMENTS

| | | | |
|---|---|---|---|
| 2,072,303 A | 3/1937 | Herrmann et al. | |
| 2,386,454 A | 10/1945 | Frosch et al. | |
| 3,773,737 A | 11/1973 | Goodman et al. | |
| 3,849,514 A | 11/1974 | Gray, Jr. et al. | |
| 4,226,243 A | 10/1980 | Shalaby et al. | |
| 4,304,767 A | 12/1981 | Heller et al. | |
| 4,329,383 A | 5/1982 | Joh | 428/36 |
| 4,343,931 A | 8/1982 | Barrows | |
| 4,529,792 A | 7/1985 | Barrows | |
| 4,611,051 A | 9/1986 | Hayes et al. | |
| 4,656,242 A | 4/1987 | Swan et al. | |
| 4,733,665 A | 3/1988 | Palmaz | 128/343 |
| 4,800,882 A | 1/1989 | Gianturco | 128/343 |
| 4,882,168 A | 11/1989 | Casey et al. | 424/468 |
| 4,886,062 A | 12/1989 | Wiktor | 128/343 |
| 4,931,287 A | 6/1990 | Bae et al. | |
| 4,941,870 A | 7/1990 | Okada et al. | 600/36 |
| 4,977,901 A | 12/1990 | Ofstead | 128/772 |
| 5,019,096 A | 5/1991 | Fox, Jr. et al. | |
| 5,100,992 A | 3/1992 | Cohn et al. | |
| 5,112,457 A | 5/1992 | Marchant | 204/165 |
| 5,133,742 A | 7/1992 | Pinchuk | |
| 5,163,952 A | 11/1992 | Froix | |
| 5,165,919 A | 11/1992 | Sasaki et al. | 424/488 |
| 5,219,980 A | 6/1993 | Swidler | |
| 5,258,020 A | 11/1993 | Froix | |
| 5,272,012 A | 12/1993 | Opolski | 428/423.1 |
| 5,292,516 A | 3/1994 | Viegas et al. | 424/423 |
| 5,298,260 A | 3/1994 | Viegas et al. | 424/486 |
| 5,300,295 A | 4/1994 | Viegas et al. | 424/427 |
| 5,306,501 A | 4/1994 | Viegas et al. | 424/423 |
| 5,306,786 A | 4/1994 | Moens et al. | |
| 5,328,471 A | 7/1994 | Slepian | 604/101 |
| 5,330,768 A | 7/1994 | Park et al. | 424/501 |
| 5,380,299 A | 1/1995 | Fearnot et al. | 604/265 |
| 5,417,981 A | 5/1995 | Endo et al. | 424/486 |
| 5,447,724 A | 9/1995 | Helmus et al. | 424/426 |
| 5,455,040 A | 10/1995 | Marchant | 424/426 |
| 5,462,990 A | 10/1995 | Hubbell et al. | 525/54.1 |
| 5,464,650 A | 11/1995 | Berg et al. | 427/2.3 |
| 5,485,496 A | 1/1996 | Lee et al. | |
| 5,516,881 A | 5/1996 | Lee et al. | |
| 5,569,463 A | 10/1996 | Helmus et al. | 424/426 |
| 5,578,073 A | 11/1996 | Haimovich et al. | 623/1 |
| 5,581,387 A | 12/1996 | Cahill | |
| 5,584,877 A | 12/1996 | Miyake et al. | |
| 5,605,696 A | 2/1997 | Eury et al. | 424/423 |
| 5,607,467 A | 3/1997 | Froix | |
| 5,609,629 A * | 3/1997 | Fearnot et al. | 623/1.42 |
| 5,610,241 A | 3/1997 | Lee et al. | |
| 5,616,338 A | 4/1997 | Fox, Jr. et al. | |
| 5,624,411 A | 4/1997 | Tuch | 604/265 |
| 5,628,730 A | 5/1997 | Shapland et al. | 604/21 |
| 5,644,020 A | 7/1997 | Timmermann et al. | |
| 5,649,977 A | 7/1997 | Campbell | 623/1 |
| 5,658,995 A | 8/1997 | Kohn et al. | 525/432 |
| 5,667,767 A | 9/1997 | Greff et al. | 424/9.411 |
| 5,670,558 A | 9/1997 | Onishi et al. | 523/112 |
| 5,674,242 A | 10/1997 | Phan et al. | |
| 5,679,400 A | 10/1997 | Tuch | 427/2.14 |
| 5,700,286 A | 12/1997 | Tartaglia et al. | 623/1 |

(Continued)

FOREIGN PATENT DOCUMENTS

DE 42 24 401 1/1994

(Continued)

OTHER PUBLICATIONS

Anonymous, *Cardiologists Draw—Up The Dream Stent*, Clinica 710:15 (Jun. 17, 1996), http://www.dialogweb.com/cgi/document?reg=1061848202959, printed Aug. 25, 2003 (2 pages).

(Continued)

*Primary Examiner*—Terressa Boykin
(74) *Attorney, Agent, or Firm*—Squire, Sanders & Dempsey L.L.P.

(57) ABSTRACT

Coatings for an implantable medical devices such as stents and methods of fabricating thereof are disclosed. The coatings comprise a biologically absorbable poly(ester amide), which is a polymeric product of a reaction between a diol-diamine and a dicarboxylic acid.

27 Claims, No Drawings

U.S. PATENT DOCUMENTS

| | | | |
|---|---|---|---|
| 5,702,754 A | 12/1997 | Zhong | 427/2.12 |
| 5,711,958 A | 1/1998 | Cohn et al. | |
| 5,716,981 A | 2/1998 | Hunter et al. | 514/449 |
| 5,721,131 A | 2/1998 | Rudolph et al. | |
| 5,723,219 A | 3/1998 | Kolluri et al. | |
| 5,735,897 A | 4/1998 | Buirge | 623/12 |
| 5,746,998 A | 5/1998 | Torchilin et al. | 424/9.4 |
| 5,759,205 A | 6/1998 | Valentini | |
| 5,776,184 A | 7/1998 | Tuch | 623/1 |
| 5,783,657 A | 7/1998 | Pavlin et al. | |
| 5,788,979 A | 8/1998 | Alt et al. | 424/426 |
| 5,800,392 A | 9/1998 | Racchini | 604/96 |
| 5,820,917 A | 10/1998 | Tuch | 427/2.1 |
| 5,824,048 A | 10/1998 | Tuch | 623/1 |
| 5,824,049 A | 10/1998 | Ragheb et al. | 623/1 |
| 5,830,178 A | 11/1998 | Jones et al. | 604/49 |
| 5,837,008 A | 11/1998 | Berg et al. | 623/1 |
| 5,837,313 A | 11/1998 | Ding et al. | 427/2.21 |
| 5,849,859 A | 12/1998 | Acemoglu | |
| 5,851,508 A | 12/1998 | Greff et al. | 424/9.411 |
| 5,854,376 A | 12/1998 | Higashi | |
| 5,858,746 A | 1/1999 | Hubbell et al. | 435/177 |
| 5,861,387 A | 1/1999 | Labrie et al. | |
| 5,865,814 A | 2/1999 | Tuch | 604/265 |
| 5,869,127 A | 2/1999 | Zhong | 427/2.12 |
| 5,873,904 A | 2/1999 | Ragheb et al. | 623/1 |
| 5,876,433 A | 3/1999 | Lunn | 623/1 |
| 5,877,224 A | 3/1999 | Brocchini et al. | 514/772.2 |
| 5,879,713 A | 3/1999 | Roth et al. | |
| 5,902,875 A | 5/1999 | Roby et al. | |
| 5,905,168 A | 5/1999 | Dos Santos et al. | |
| 5,910,564 A | 6/1999 | Gruning et al. | |
| 5,914,387 A | 6/1999 | Roby et al. | |
| 5,919,893 A * | 7/1999 | Roby et al. | 528/310 |
| 5,925,720 A | 7/1999 | Kataoka et al. | 525/523 |
| 5,932,299 A | 8/1999 | Katoot | |
| 5,955,509 A | 9/1999 | Webber et al. | 514/772.7 |
| 5,958,385 A | 9/1999 | Tondeur et al. | |
| 5,962,138 A | 10/1999 | Kolluri et al. | |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | 605/265 |
| 6,010,530 A | 1/2000 | Goicoechea | 623/1 |
| 6,011,125 A | 1/2000 | Lohmeijer et al. | |
| 6,015,541 A | 1/2000 | Greff et al. | 424/1.25 |
| 6,033,582 A | 3/2000 | Lee et al. | 216/37 |
| 6,034,204 A | 3/2000 | Mohr et al. | |
| 6,042,875 A | 3/2000 | Ding et al. | 427/2.24 |
| 6,051,576 A | 4/2000 | Ashton et al. | 514/255 |
| 6,051,648 A | 4/2000 | Rhee et al. | 525/54.1 |
| 6,054,553 A | 4/2000 | Groth et al. | |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | 514/781 |
| 6,080,488 A | 6/2000 | Hostettler et al. | 428/423.3 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,120,491 A | 9/2000 | Kohn et al. | |
| 6,120,536 A | 9/2000 | Ding et al. | 623/1.43 |
| 6,120,788 A | 9/2000 | Barrows | |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,136,333 A | 10/2000 | Cohn et al. | |
| 6,143,354 A | 11/2000 | Koulik et al. | |
| 6,153,252 A | 11/2000 | Hossainy et al. | 427/2.3 |
| 6,159,978 A | 12/2000 | Myers et al. | |
| 6,165,212 A | 12/2000 | Dereume et al. | 623/1.13 |
| 6,172,167 B1 | 1/2001 | Stapert et al. | |
| 6,177,523 B1 | 1/2001 | Reich et al. | |
| 6,180,632 B1 | 1/2001 | Myers et al. | |
| 6,203,551 B1 | 3/2001 | Wu | 606/108 |
| 6,211,249 B1 | 4/2001 | Cohn et al. | |
| 6,214,901 B1 | 4/2001 | Chudzik et al. | |
| 6,231,600 B1 | 5/2001 | Zhong | 623/1.42 |
| 6,240,616 B1 | 6/2001 | Yan | 29/527.2 |
| 6,245,753 B1 | 6/2001 | Byun et al. | 514/56 |
| 6,245,760 B1 | 6/2001 | He et al. | |
| 6,248,129 B1 | 6/2001 | Froix | |
| 6,251,136 B1 | 6/2001 | Guruwaiya et al. | 623/1.46 |
| 6,254,632 B1 | 7/2001 | Wu et al. | 623/1.15 |
| 6,258,121 B1 | 7/2001 | Yang et al. | 623/1.46 |
| 6,258,371 B1 | 7/2001 | Koulik et al. | |
| 6,262,034 B1 | 7/2001 | Mathiowitz et al. | |
| 6,270,788 B1 | 8/2001 | Koulik et al. | |
| 6,277,449 B1 | 8/2001 | Kolluri et al. | |
| 6,283,947 B1 | 9/2001 | Mirzaee | 604/264 |
| 6,283,949 B1 | 9/2001 | Roorda | 604/288.02 |
| 6,284,305 B1 | 9/2001 | Ding et al. | 427/2.28 |
| 6,287,628 B1 | 9/2001 | Hossainy et al. | 427/2.3 |
| 6,299,604 B1 | 10/2001 | Ragheb et al. | 604/265 |
| 6,306,176 B1 | 10/2001 | Whitbourne | 623/23.59 |
| 6,331,313 B1 | 12/2001 | Wong et al. | 424/427 |
| 6,335,029 B1 | 1/2002 | Kamath et al. | 424/423 |
| 6,344,035 B1 | 2/2002 | Chudzik et al. | |
| 6,346,110 B2 | 2/2002 | Wu | 606/108 |
| 6,358,556 B1 | 3/2002 | Ding et al. | 427/2.24 |
| 6,379,381 B1 | 4/2002 | Hossainy et al. | 623/1.42 |
| 6,387,379 B1 | 5/2002 | Goldberg et al. | |
| 6,395,326 B1 | 5/2002 | Castro et al. | 427/2.24 |
| 6,419,692 B1 | 7/2002 | Yang et al. | 623/1.15 |
| 6,451,373 B1 | 9/2002 | Hossainy et al. | 427/2.25 |
| 6,482,834 B2 | 11/2002 | Spada et al. | |
| 6,494,862 B1 | 12/2002 | Ray et al. | 604/96.01 |
| 6,503,538 B1 | 1/2003 | Chu et al. | |
| 6,503,556 B2 | 1/2003 | Harish et al. | 427/2.24 |
| 6,503,954 B1 | 1/2003 | Bhat et al. | 514/772.2 |
| 6,506,437 B1 | 1/2003 | Harish et al. | 427/2.25 |
| 6,524,347 B1 | 2/2003 | Myers et al. | |
| 6,527,801 B1 | 3/2003 | Dutta | 623/1.46 |
| 6,527,863 B1 | 3/2003 | Pacetti et al. | 118/500 |
| 6,528,526 B1 | 3/2003 | Myers et al. | |
| 6,530,950 B1 | 3/2003 | Alvarado et al. | |
| 6,530,951 B1 | 3/2003 | Bates et al. | |
| 6,540,776 B2 | 4/2003 | Sanders Millare et al. | 623/1.15 |
| 6,544,223 B1 | 4/2003 | Kokish | 604/103.01 |
| 6,544,543 B1 | 4/2003 | Mandrusov et al. | 424/422 |
| 6,544,582 B1 | 4/2003 | Yoe | 427/2.24 |
| 6,555,157 B1 | 4/2003 | Hossainy | 427/2.24 |
| 6,558,733 B1 | 5/2003 | Hossainy et al. | 427/2.24 |
| 6,565,659 B1 | 5/2003 | Pacetti et al. | 118/500 |
| 6,572,644 B1 | 6/2003 | Moein | 623/1.11 |
| 6,585,755 B2 | 7/2003 | Jackson et al. | |
| 6,585,765 B1 | 7/2003 | Hossainy et al. | 623/1.45 |
| 6,585,926 B1 | 7/2003 | Mirzaee | 264/400 |
| 6,616,765 B1 | 9/2003 | Hossainy et al. | |
| 6,623,448 B2 | 9/2003 | Slater | |
| 6,625,486 B2 | 9/2003 | Lundkvist et al. | |
| 6,645,135 B1 | 11/2003 | Bhat | |
| 6,645,195 B1 | 11/2003 | Bhat et al. | |
| 6,656,216 B1 | 12/2003 | Hossainy et al. | |
| 6,656,506 B1 | 12/2003 | Wu et al. | |
| 6,660,034 B1 | 12/2003 | Mandrusov et al. | |
| 6,663,662 B2 | 12/2003 | Pacetti et al. | |
| 6,663,880 B1 | 12/2003 | Roorda et al. | |
| 6,666,880 B1 | 12/2003 | Chiu et al. | |
| 6,673,154 B1 | 1/2004 | Pacetti et al. | |
| 6,673,385 B1 | 1/2004 | Ding et al. | |
| 6,689,099 B2 | 2/2004 | Mirzaee | |
| 6,695,920 B1 | 2/2004 | Pacetti et al. | |

| | | |
|---|---|---|
| 6,703,040 B2 | 3/2004 | Katsarava et al. |
| 6,706,013 B1 | 3/2004 | Bhat et al. |
| 6,709,514 B1 | 3/2004 | Hossainy |
| 6,712,845 B2 | 3/2004 | Hossainy |
| 6,713,119 B2 | 3/2004 | Hossainy et al. |
| 6,716,444 B1 | 4/2004 | Castro et al. |
| 6,723,120 B2 | 4/2004 | Yan |
| 6,733,768 B2 | 5/2004 | Hossainy et al. |
| 6,740,040 B1 | 5/2004 | Mandrusov et al. |
| 6,743,462 B1 | 6/2004 | Pacetti et al. |
| 6,749,626 B1 | 6/2004 | Bhat et al. |
| 6,753,071 B1 | 6/2004 | Pacetti et al. |
| 6,758,859 B1 | 7/2004 | Dang et al. |
| 6,759,054 B2 | 7/2004 | Chen et al. |
| 6,764,505 B1 | 7/2004 | Hossainy et al. |
| 6,770,725 B2 * | 8/2004 | Santerre .................. 528/29 |
| 2001/0007083 A1 | 7/2001 | Roorda |
| 2001/0014717 A1 | 8/2001 | Hossainy et al. |
| 2001/0018469 A1 | 8/2001 | Chen et al. ............. 523/121 |
| 2001/0020011 A1 | 9/2001 | Mathiowitz et al. |
| 2001/0029351 A1 | 10/2001 | Falotico et al. |
| 2001/0037145 A1 | 11/2001 | Guruwaiya et al. ........ 623/1.15 |
| 2001/0051608 A1 | 12/2001 | Mathiowitz et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0071822 A1 | 6/2002 | Uhrich |
| 2002/0077693 A1 | 6/2002 | Barclay et al. ............ 623/1.13 |
| 2002/0082679 A1 | 6/2002 | Sirhan et al. |
| 2002/0087123 A1 | 7/2002 | Hossainy et al. |
| 2002/0091433 A1 | 7/2002 | Ding et al. ................. 623/1.2 |
| 2002/0094440 A1 | 7/2002 | Llanos et al. |
| 2002/0111590 A1 | 8/2002 | Davila et al. |
| 2002/0120326 A1 | 8/2002 | Michal |
| 2002/0123801 A1 | 9/2002 | Pacetti et al. |
| 2002/0142039 A1 | 10/2002 | Claude |
| 2002/0155212 A1 | 10/2002 | Hossainy .................. 427/2.25 |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065377 A1 | 4/2003 | Davila et al. .............. 623/1.13 |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman .................. 424/486 |
| 2003/0105518 A1 | 6/2003 | Dutta |
| 2003/0113439 A1 | 6/2003 | Pacetti et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy et al. |
| 2003/0207020 A1 | 11/2003 | Villareal |
| 2003/0211230 A1 | 11/2003 | Pacetti et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |
| 2005/0106204 A1 * | 5/2005 | Hossainy et al. ........... 424/423 |
| 2005/0112171 A1 * | 5/2005 | Tang et al. ................. 424/423 |

FOREIGN PATENT DOCUMENTS

| | | |
|---|---|---|
| DE | 19652037 | 6/1998 |
| EP | 0 301 856 | 2/1989 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| SU | EP 0 396 429 | 11/1990 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/03218 | 1/1998 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |

| | | |
|---|---|---|
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 2004/000383 | 12/2003 |
| WO | WO 2004/009145 | 1/2004 |

OTHER PUBLICATIONS

Anonymous, *Heparin-coated stents cut complications by 30%*, Clinica 732:17 (Nov. 18, 1996), http://www.dialogweb.com/cgi/document?reg=1061847871753, printed Aug. 25, 2004 (2 pages).
Anonymous, *Rolling Therapeutic Agent Loading Device for Therapeutic Agent Delivery of Coated Stent* (Abstract 434009), Res. Disclos. pp. 974-975 (Jun. 2000).
Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).
Aoyagi et al., *Preparation of cross-linked aliphatic polyester and application to thermo-responsive material*, Journal of Controlled Release 32:87-96 (1994).
Barath et al., *Low Dose of Antitumor Agents Prevents Smooth Muscle Cell Proliferation After Endothelial Injury*, JACC 13(2): 252A (Abstract) (Feb. 1989).
Barbucci et al., *Coating of commercially available materials with a new heparinizable material*, J. Biomed. Mater. Res. 25:1259-1274 (Oct. 1991).
Chung et al., *Inner core segment design for drug delivery control of thermo-responsive polymeric micelles*, Journal of Controlled Release 65:93-103 (2000).
Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).
Dichek et al., *Seeding of Intravascular Stents with Genetically Engineered Endothelial Cells*, Circ. 80(5):1347-1353 (Nov. 1989).
Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).
Helmus, *Overview of Biomedical Materials*, MRS Bulletin, pp. 33-38 (Sep. 1991).
Herdeg et al., *Antiproliferative Stent Coatings: Taxol and Related Compounds*, Semin. Intervent. Cardiol. 3:197-199 (1998).
Inoue et al., *An AB block copolymer of oligo(methyl methacrylate) and poly(acrylic acid) for micellar delivery of hydrophobic drugs*, Journal of Controlled Release 51:221-229 (1998).
Kataoka et al., *Block copolymer micelles as vehicles for drug delivery*, Journal of Controlled Release 24:119-132 (1993).
Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).
Liu et al., *Drug release characteristics of unimolecular polymeric micelles*, Journal of Controlled Release 68:167-174 (2000).
Marconi et al., *Covalent bonding of heparin to a vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).
Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).
Miyazawa et al., *Effects of Pemirolast and Tranilast on Intimal Thickening After Arterial Injury in the Rat*, J. Cardiovasc. Pharmacol., pp. 157-162 (1997).
Nordrehaug et al., *A novel biocompatible coating applied to coronary stents*, European Heart Journal 14, p. 321 (P1694), Abstr. Suppl. (1993).
Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).
Ozaki et al., *New Stent Technologies*, Progress in Cardiovascular Diseases, vol. XXXIX(2):129-140 (Sep./Oct. 1996).
Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).
Peng et al., *Role of polymers in improving the results of stenting in coronary arteries*, Biomaterials 17:685-694 (1996).
Shigeno, *Prevention of Cerebrovascular Spasm By Bosentan, Novel Endothelin Receptor*, Chemical Abstract 125:212307 (1996).
van Beusekom et al., *Coronary stent coatings*, Coronary Artery Disease 5(7):590-596 (Jul. 1994).
Wilensky et al., *Methods and Devices for Local Drug Delivery in Coronary and Peripheral Arteries*, Trends Cardiovasc. Med. 3(5): 163-170 (1993).
Yokoyama et al., *Characterization of physical entrapment and chemical conjugation of adriamycin in polymeric micelles and their design for in vivo delivery to a solid tumor*, Journal of Controlled Release 50:79-92 (1998).
International Search Report and Written Opinion for the PCT/US2004/040957 filed Dec. 7, 2004, mailed Apr. 29, 2005, 12 pgs.
Chandrasekar et al., *Coronary Artery Endothelial Protection After Local Delivery of 17β-Estradiol During Balloon Angioplasty in a Porcine Model: A Potential New Pharmacologic Approach to Improve Endothelial Function*, J. of Am. College of Cardiology, vol. 38, No. 5, (2001) pp. 1570-1576.
De Lezo et al., *Intracoronary Ultrasound Assessment of Directional Coronary Atherectomy: Immediate and Follow-Up Findings*, JACC vol. 21, No. 2, (1993) pp. 298-307.
Huang et al., *Biodegradable Polymers Derived from Aminoacids*, Macromol. Symp. 144, 7-32 (1999).
Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).
Moreno et al., *Macrophage Infiltration Predicts Restenosis After Coronary Intervention in Patients with Unstable Angina*, Circulation, vol. 94, No. 12, (1996) pp. 3098-3102.
Oikawa et al., Mechanisms of Acute Gain and Late Lumen Loss After Atherectomy in Different Preintervention Arterial Remodeling Patterns, *The Am. J. of Cardilogy*, vol. 89, (2002) pp. 505-510.
Saotome, et al., *Novel Enzymatically Degradable Polymers Comprising α-Amino Acid, 1,2-Ethanediol, and Adipic Acid*, Chemistry Letters, pp. 21-24, (1991).
Scully et al., *Effect of a heparan sulphate with high affinity for antithrombin III upon inactivation of thrombin and coagulation Factor Xa*, Biochem J. 262, (1989) pp. 651-658.
Virmani et al., *Lessons From Sudden Coronary Death a Comprehensive Morphological Classification Scheme for Atherosclerotic Lesions*, Arterioscler Thromb Vasc Biol. (2000) pp. 1262-1275.

\* cited by examiner

BIOLOGICALLY ABSORBABLE COATINGS FOR IMPLANTABLE DEVICES BASED ON POLY(ESTER AMIDES) AND METHODS FOR FABRICATING THE SAME

BACKGROUND

1. Field of the Invention

This invention is directed to coatings for drug delivery devices, such as drug eluting vascular stents, and methods for producing the same.

2. Description of the State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

Stents are used not only as a mechanical intervention but also as a vehicle for providing pharmacological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents which have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

Pharmacological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results. One proposed method for medicating stents involves the use of a polymeric carrier coated onto the surface of a stent. A solution which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer.

Poly(ester amides) as described in U.S. Pat. No. 6,503,538 to Chu et al. are a category of polymers that are well suited for stent coatings. Poly(ester amides) are very biocompatible and are an effective matrix for delivery of drugs. However, improvements can be made to the properties of poly(ester amides). For example, the poly(ester amides) described by Chu et al. are too soft and tacky causing these poly(ester amides) to adhere to balloon surfaces. In addition, the poly(ester amides) described by Chu et al. tend to flow during ethylene oxide (ETO) sterilization process. Accordingly, there is a need to have poly(ester amides) with improved hardness, increased ability not to adhere to balloon surfaces and higher degree of resistance to flow during the process of ETO sterilization.

SUMMARY

A medical article comprising an implantable substrate having a coating is provided, the coating includes a polymeric product of a reaction between a diol-diamine and a dicarboxylic acid. The diol-diamine can be a product of condensation of an amino acid and a diol. Examples of amino acids that can be used for making the diol-diamine include glycine, alanine, valine, isoleucine, leucine, phenyl alanine, methionine, asparagine, glutamine, proline, and mixtures thereof. Examples of diols that can be used for making the diol-diamine include ethylene glycol, 1,2-propanediol, 1,3-propanediol, 1,4-butane diol, 1,5-pentanediol, 1,6-hexanediol, 1,7-heptanediol, 1,8-octanediol, 1,9-nonanediol, 1,10-decanediol, 1,11-undecanediol, and 1,12-dodecanediol, and mixtures thereof. Examples of dicarboxylic acids that can be used for reacting with the diol-diamine include oxalic acid, malonic acid, succinic acid, glutaric acid, adipic acid, pimelic acid, suberic acid, azelaic acid, sebacic acid, undecanedioic acid, dodecanedioic acid, brassylic acid, tetradecanedioic acid, pentadecanedioic acid, thapsic acid, and mixtures thereof.

A medical article comprising an implantable substrate having a coating is provided, the coating includes a condensation copolymer having a formula

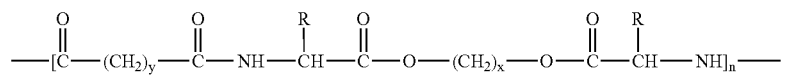

wherein R is selected from a group consisting of hydrogen; methyl, iso-propyl, sec-butyl, iso-butyl, benzyl, methyl mercaptoethyl, methylene amide, and ethylene amide; x is an integer having a value between 2 and 16; y is an integer having a value between 0 and 16; and n is an integer having a value between 35 and 1,100.

A medical article comprising an implantable substrate having a coating is provided, the coating includes a condensation copolymer having a formula

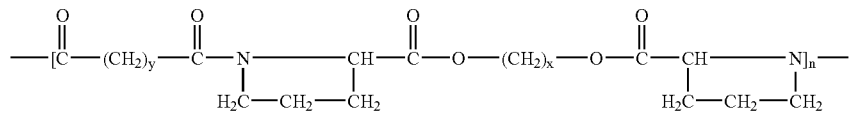

wherein x is an integer having a value between 2 and 16; y is an integer having a value between 0 and 16; and n is an integer having a value between 35 and 1,100.

A method for fabricating a medical article is provided, the method includes synthesizing a condensation copolymer and forming a coating comprising the copolymer on at least a portion of an implantable substrate, the synthesizing of the copolymer including reacting a diol-diamine with a dicarboxylic acid.

A method for fabricating a medical article is provided, the method includes synthesizing a condensation copolymer, and forming a coating comprising the copolymer on at least a portion of an implantable substrate, wherein the condensation copolymer has a formula

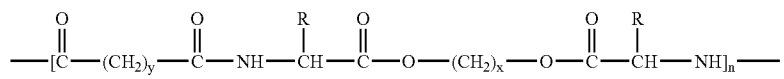

wherein R is selected from a group consisting of hydrogen; methyl, iso-propyl, sec-butyl, iso-butyl, benzyl, methyl mercaptoethyl, methylene amide, and ethylene amide; x is an integer having a value between 2 and 16; y is an integer having a value between 0 and 16; and n is an integer having a value between 35 and 1,100.

A method for fabricating a medical article is provided, the method includes synthesizing a condensation copolymer, and forming a coating based on the copolymer on at least a portion of an implantable substrate, wherein the condensation copolymer has a formula

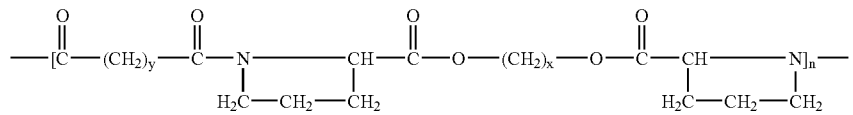

wherein x is an integer having a value between 2 and 16; y is an integer having a value between 0 and 16; and n is an integer having a value between 35 and 1,100.

DETAILED DESCRIPTION

1. TERMS AND DEFINITIONS

The following definitions apply:

The term "biologically absorbable" coatings and/or polymers is defined as coatings and/or polymers that are capable of being completely degraded, dissolved, and/or eroded when exposed to bodily fluids such as blood and are gradually resorbed, absorbed and/or eliminated by the body. The processes of breaking down and eventual absorption and elimination of the coating and/or polymer can be caused, for example, by hydrolysis, enzymatic action, oxidation, phagocytosis, metabolic processes, bulk or surface erosion, and the like.

Whenever the reference is made to "biologically absorbable" stent coatings and/or polymers forming such stent coatings, it is understood that after the process of degradation, dissolution, erosion, absorption, and/or resorption has been completed, no coating will remain on the stent.

The term "poly(ester amide)" or "PEA" is defined as a polymer having at least one ester bond (I) and at least one amide bond (II):

 (I)

 (II)

The term "condensation copolymer" is defined as a copolymer that is a product of a process of polycondensation of two monomers. "Polycondensation" is defined in accordance with the definition used by the IUPAC (the International Union for Pure and Applied Chemistry." The IUPAC defines "polycondensation" as a process of polymerization in which the growth of polymer chains proceeds by condensation reactions between molecules of all degrees of polymerization (Definition 3.7).

2. EMBODIMENTS OF THE INVENTION

A coating for an implantable medical device, such as a stent, according to embodiments of the present invention, can be a multi-layer structure that can include any of the following four layers or any combination thereof:

(a) a primer layer;

(b) a drug-polymer layer (also referred to as "reservoir" or "reservoir layer"), comprising a condensation copolymer and a drug, or, alternatively, a polymer free drug layer;

(c) a topcoat layer; and/or (d) a finishing coat layer.

Any of the layers of the stent coating can be formed on the stent by dissolving the condensation copolymer or a blend of condensation copolymers in a solvent, or a mixture of solvents, and applying the resulting copolymer solution on the stent by spraying or immersing the stent in the solution. After the solution has been applied onto the stent, the coating is dried by allowing the solvent to evaporate. The process of drying can be accelerated if the drying is conducted at an elevated temperature.

To incorporate a drug into the reservoir layer, the drug can be combined with the copolymer solution that is applied onto the stent as described above. Alternatively, to fabricate a polymer free reservoir, the drug can be dissolved in a suitable solvent or mixture of solvents, and the resulting drug solution can be applied on the stent by spraying or immersing the stent in the drug solution.

Instead of introducing the drug as a solution, the drug can be introduced as a colloidal system, such as a suspension in an appropriate solvent phase. To make the suspension, the drug can be dispersed in the solvent phase using conventional techniques used in colloid chemistry. Depending on a variety of factors, e.g., the nature of the drug, those having ordinary skill in the art can select the solvent to form the solvent phase of the suspension, as well as the quantity of the drug to be dispersed in the solvent phase. The suspension can be mixed with a condensation copolymer solution and the mixture can be applied on the stent as described above. Alternatively, the drug suspension can be applied on the stent without being mixed with the copolymer solution.

The drug-polymer layer can be applied directly onto at least a part of the stent surface to serve as a reservoir for at least one active agent or a drug which is incorporated into the reservoir layer. The primer layer can be applied between the stent and the reservoir to improve the adhesion of the drug-polymer layer to the stent. The topcoat layer can be applied over at least a portion of the reservoir layer and serves as a rate limiting membrane which helps to control the rate of release of the drug. In one embodiment, the topcoat layer can be essentially free from any active agents or drugs. If the topcoat layer is used, the optional finishing coat layer can be applied over at least a portion of the topcoat layer for further control of the drug release rate and for improving the biocompatibility of the coating, for example, for providing the surface of the coating with anti-thrombotic and/or non-fouling properties. Without the topcoat layer, the finishing coat layer can be deposited directly on the reservoir layer.

In one embodiment, any or all of the layers of the stent coating, can be made of a condensation copolymer that is both biologically beneficial and biologically degradable, erodable, absorbable, and/or resorbable polymer. In another embodiment, just the outermost layer of the coating can be limited to such a polymer.

To illustrate in more detail, in the stent coating having all four layers described above (i.e., the primer, the reservoir layer, the topcoat layer and the finishing coat layer), the outermost layer is the finishing coat layer, which is made of a condensation copolymer that is biologically degradable, erodable, absorbable, and/or resorbable. In this case, optionally, the remaining layers (i.e., the primer, the reservoir layer, the topcoat layer) can be also fabricated of a biologically degradable condensation copolymer; and the copolymer can be the same or different in each layer.

If the finishing coat layer is not used, the topcoat layer can be the outermost layer and is made of a biologically degradable condensation copolymer. In this case, optionally, the remaining layers (i.e., the primer and the reservoir layer) can be also fabricated of a biologically degradable condensation copolymer; and the copolymer can be the same or different in each of the three layers.

If neither the finishing coat layer nor the topcoat layer is used, the stent coating can have two layers, the primer and the reservoir. The reservoir in this case is the outermost layer of the stent coating and can be made of a biologically degradable condensation copolymer. Optionally, the primer can be also fabricated of a biologically degradable condensation copolymer. The two layers can be made from the same or different materials.

Biologically absorbable condensation copolymers that can be used for making any of the stent coating layers include poly(ester amides) (PEA). The synthetic techniques that can be used for obtaining the PEAs are described below. Generally, the PEAs are products of reaction between one precursor-reagent of group A and one precursor-reagent of group B. According to embodiments of this invention, the precursor-reagents of group A include various diol-diamines, and the precursor-reagents of group B include various dicarboxylic acids. In some embodiments, the coating can be free from any particular poly(ester amide).

The precursor-reagents of groups A and B are characterized as follows.

A. Group A Reagents—Diol-Diamines

The diol-diamines comprising group A precursor-reagents (hereinafter, "reagents") that can be used according to embodiments of the present invention are chemical compounds having a general formula (III):

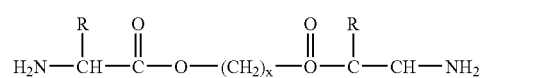

(III)

wherein R can be hydrogen, methyl, iso-propyl, sec-butyl, iso-butyl, benzyl, methyl mercaptoethyl ($CH_2$—$CH_2$—S—$CH_3$), methylene amide ($CH_2$—CO—$NH_2$), or ethylene amide ($CH_2$—$CH_2$—CO—$NH_2$), and x can be an integer between 2 and 16.

The reagents described by formula (III) are diol-diamines that can be synthesized by condensation of an amino acid and a diol. The synthesis can be carried under the conditions favoring esterification of the amino acid via the amino acid's carboxyl group. The reaction can be conducted under dehydrating conditions which include anhydrous environment and an elevated temperature, for example, about 50° C. The reaction can be catalyzed by a strong acid or base, e.g., p-toluenesulfonic acid. Anhydrous conditions can be obtained by the removal of water via an azeotropic distillation of the reaction solvent, e.g., toluene or benzene.

The diol that can be used to make diol-diamines having formula (III) has the formula HO—$(CH_2)_x$—OH, where x is defined above. Representative examples of diols that can be used include ethylene glycol, 1,2-propanediol, 1,3-propanediol, 1,4-butane diol, 1,5-pentanediol, 1,6-hexanediol, 1,7-heptanediol, 1,8-octanediol, 1,9-nonanediol, 1,10-decanediol, 1,11-undecanediol, 1,12-dodecanediol, or mixtures thereof.

The amino acid that can be used to prepare diol-diamines having formula (III) has the formula $H_2N-CHR-COOH$, where R is defined above. Some amino acids that can be used are summarized in Table 1.

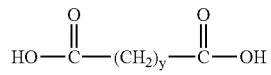
(IV)

TABLE 1

Amino Acid ($H_2N-CHR-COOH$)

| No. | R | Formula | Name |
|---|---|---|---|
| 1 | H | $H_2N-CH_2-COOH$ | glycine (aminoethanoic acid) |
| 2 | $CH_3$ | $H_2N-CH(CH_3)-COOH$ | alanine (2-aminopropanoic acid) |
| 3 | $i-C_3H_7$ | $H_2N-CH(CH(CH_3)_2)-COOH$ | valine (2-amino-3-methyl butyric acid) |
| 4 | $sec-C_4H_9$ | $H_2N-CH(CH(CH_3)CH_2CH_3)-COOH$ | isoleucine (2-amino-3-methyl pentanoic acid) |
| 5 | $i-C_4H_9$ | $H_2N-CH(CH_2CH(CH_3)_2)-COOH$ | leucine (2-amino-4-methyl pentanoic acid) |
| 6 | $C_6H_5-CH_2$ | $H_2N-CH(CH_2C_6H_5)-COOH$ | phenylalanine (2-amino-3-phenylpropanoic acid) |
| 7 | $(CH_2)_2-S-CH_3$ | $H_2N-CH(CH_2CH_2SCH_3)-COOH$ | methionine (α-amino-γ-methylmercaptobutyric acid) |
| 8 | $CH_2-CO-NH_2$ | $H_2N-CH(CH_2CONH_2)-COOH$ | asparagine (2,4-diamino-4-oxobutanoic acid) |
| 9 | $(CH_2)_2-CO-NH_2$ | $H_2N-CH(CH_2CH_2CONH_2)-COOH$ | glutamine (2,5-diamino-4-oxopentanoic acid) |

In addition to amino acids listed in Table 2, alternatively other amino acids can be for example, proline (2-pyrrolidine carboxylic acid).

Either one amino acid or two different amino acids can be used to synthesize the diol-diamines. If one amino acid is used, two molar equivalents of the amino acid can be used per one molar equivalent of a diol to form diol-diamines having formula (III) described above. If two different amino acids are used, one molar equivalent of the first amino acid plus one molar equivalent of the second amino acid are used per one molar equivalent of a diol.

B. Group B Reagents—Dicarboxylic Acids

The dicarboxylic acid comprising group B reagents that can be used for synthesizing the biologically absorbable condensation copolymers according to embodiments of the present invention are chemical compounds having a general formula (IV):

wherein y can be an integer between 0 and 16. Some examples of dicarboxylic acids described by formula (IV) that can be used are summarized in Table 2. Mixtures of the carboxylic acids presented in Table 2 can be also used, if desired.

TABLE 2

Dicarboxylic Acid ($HOOC-(CH_2)_y-COOH$)

| No. | y | Formula | Name |
|---|---|---|---|
| 1 | 0 | $HOOC-COOH$ | oxalic (ethanedioic) acid |
| 2 | 1 | $HOOC-CH_2-COOH$ | malonic (propanedioic) |
| 3 | 2 | $HOOC-(CH_2)_2-COOH$ | succinic (butanedioic) acid |
| 4 | 3 | $HOOC-(CH_2)_3-COOH$ | glutaric (pentanedioic) acid |
| 5 | 4 | $HOOC-(CH_2)_4-COOH$ | adipic (hexanedioic) acid |
| 6 | 5 | $HOOC-(CH_2)_5-COOH$ | pimelic (heptanedioic) acid |
| 7 | 6 | $HOOC-(CH_2)_6-COOH$ | suberic (octanedioic) acid |
| 8 | 7 | $HOOC-(CH_2)_7-COOH$ | azelaic (nonanedioic) acid |
| 9 | 8 | $HOOC-(CH_2)_8-COOH$ | sebacic (decanedioic) acid |

TABLE 2-continued

| | | Dicarboxylic Acid (HOOC—(CH$_2$)$_y$—COOH) | |
|---|---|---|---|
| No. | y | Formula | Name |
| 10 | 9 | HOOC—(CH$_2$)$_9$—COOH | nonane-1,9-dicarboxylic (undecanedioic) acid |
| 11 | 10 | HOOC—(CH$_2$)$_{10}$—COOH | decane-1,10-dicarboxylic (dodecanedioic) acid |
| 12 | 11 | HOOC—(CH$_2$)$_{11}$—COOH | brassylic (tridecanedioic) acid |
| 13 | 12 | HOOC—(CH$_2$)$_{12}$—COOH | dodecane-1,12-dicarboxylic (tetradecanedioic) acid |
| 14 | 13 | HOOC—(CH$_2$)$_{13}$—COOH | tridecane-1,13-dicarboxylic (pentadecanedioic) acid |
| 15 | 14 | HOOC—(CH$_2$)$_{14}$—COOH | thapsic (hexadecanedioic) acid |

As mentioned above, to synthesize the PEAs, at least one reagent of group A can be reacted with at least one reagent of group B. Coupling the diol-diamines directly with the dicarboxylic acids can be accomplished by using acid or catalysis under dehydrating conditions. To conduct the process of coupling with fewer side reactions, the dicarboxylic acid can be preliminarily activated with a carbodiimide, such as 1,3-dicyclohexylcarbodiimide (DCC), or 1-(3-dimethylaminopropyl)-3-ethylcarbodiimide hydrochloride (EDC). Alternatively, instead of a dicarboxylic acid, a derivative thereof, such as diacid chloride, diacid bromide, or p-nitrophenol derivative, can be used.

According to one embodiment, as a result of the synthesis, biologically absorbable PEAs having a general formula (V) can be obtained:

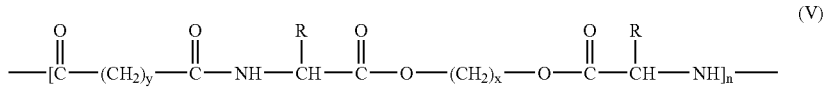

(V)

wherein R, x, and y are as defined above, and n is an integer having a value between about 35 and about 1,100, for example, between 90 and 650.

According to another embodiment, if the amino acid that is used is proline, biologically absorbable PEAs having a general formula (VI) can be obtained:

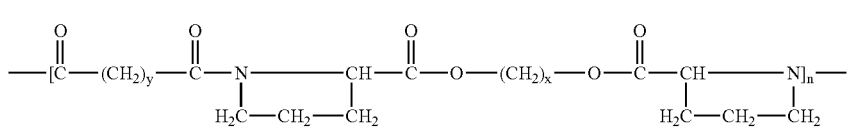

(VI)

wherein x, y, and n are as defined above.

One example of the process of synthesis of poly(ester amide) having general formula (V), can be the synthesis of the poly(ester amide) based on alanine, adipic acid, and 1,6-hexanediol according to the following procedure.

First, two equivalents of L-alanine can be combined in the benzene solution with one equivalent of 1,6-hexanediol, and with at least two equivalents of p-toluenesulphonic acid. Instead of benzene, toluene or chloroform can be used, if desired. The mixture can be heated to reflux and azeotropic distillation utilizing a Dean-Stark trap can be used to remove generated water. As a result, the di-p-toluenesulphonic acid salt of the bis-(L-alanine)-1,6-hexylene diester (monomer 1) can be obtained.

Next, adipic acid can be activated by reacting one equivalent of adipoyl chloride with two equivalents of p-nitrophenol, in the tetrahydrofuran (THF) solution, with at least two equivalents of triethylamine, to obtain di-p-nitrophenyl adipate (monomer 2). Instead of THF, diethylether or p-dioxane can be used, if desired. Both monomer 1 and monomer 2 can have stoichiometry as close as to 1:1 as possible in order to reach high molecular weights.

Finally, one equivalent of monomer 1 can be reacted with one equivalent of monomer 2 and at least two equivalents of triethylamine in dry N,N-dimethylacetamide (DMAC). Alternatively, dimethylformamide (DMF) or dimethylsulfoxide (DMSO) can be used instead of DMAC. The ratio of monomers 1 and 2 can, but need not, be 1:1. Generally, the molar ratio of the two monomers is within 10% of each other, depending on the desired molecular weight of the final polymer. The ratio can deviate from 1:1, but in case of deviation the polymerization stops at a lower molecular weight.

After combining the reactants at room temperature, the mixture can be heated with stirring at about 80° C. for about 16 hours. The viscous reaction mixture can be cooled to room temperature, diluted with a quantity of alcohol (such as methanol or ethanol) at least equal to the reaction volume, and poured into water. As a result, the final polymer, co-poly-[N,N'-adipoyl-bis-(L-alanine)-1,6-hexylene diester] can be produced. The precipitated polymer can be isolated, washed with water, and dried under vacuum.

Any layer of the stent coating can contain any amount of the biologically absorbable condensation copolymers described above, or a blend of more than one of such copolymers. If less than 100% of the layer is made of the biologically absorbable condensation copolymers described above, alternative polymers can comprise the balance. It is preferred that the alternative polymer be biodegradable but it can also be non-biodegradable. Examples of the alternative polymers that can be used include polyacrylates, such as poly(butyl methacrylate), poly(ethyl methacrylate), and poly(ethyl methacrylate-co-butyl methacrylate), and fluorinated polymers and/or copolymers, such as poly(vinylidene fluoride) and poly(vinylidene fluoride-co-hexafluoro propene), poly(N-vinyl pyrrolidone), poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-cotrimethylene carbonate), polyphosphoester, polyphosphoester urethane, poly(amino acids), cyanoacrylates, poly(trimethylene carbonate), poly(iminocarbonate), co-poly (ether-esters), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alpha-olefin copolymers, vinyl halide polymers and copolymers (such as polyvinyl chloride), polyvinyl ethers (such as polyvinyl methyl ether), polyvinylidene chloride, polyacrylonitrile, polyvinyl ketones, polyvinyl aromatics (such as polystyrene), polyvinyl esters (such as polyvinyl acetate), copolymers of vinyl monomers with each other and olefins, e.g., poly(ethylene-co-vinyl alcohol) (EVAL), ethylene-methyl methacrylate copolymers, acrylonitrile-styrene copolymers, ABS resins, and ethylene-vinyl acetate copolymers; polyamides (such as Nylon 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Representative examples of some solvents suitable for making the stent coatings include DMAC, DMF, THF, 100% absolute ethanol, cyclohexanone, xylene, toluene, acetone, i-propanol, methyl ethyl ketone, propylene glycol monomethyl ether, methyl butyl ketone, ethyl acetate, n-butyl acetate, and dioxane. Some solvent mixtures can be used as well. Representative examples of the mixtures include:

(1) DMAC and methanol (e.g., a 50:50 by mass mixture);
(2) water, i-propanol, and DMAC (e.g., a 10:3:87 by mass mixture);
(3) i-propanol, and DMAC (e.g., 80:20, 50:50, or 20:80 by mass mixtures);
(4) acetone and cyclohexanone (e.g., 80:20, 50:50, or 20:80 by mass mixtures);
(5) acetone and xylene (e.g. a 50:50 by mass mixture);
(6) acetone, FLUX REMOVER AMS, and xylene (e.g., a 10:50:40 by mass mixture); and
(7) 1,1,2-trichloroethane and chloroform (e.g., a 80:20 by mass mixture).

FLUX REMOVER AMS is trade name of a solvent manufactured by Tech Spray, Inc. of Amarillo, Tex. comprising about 93.7% of a mixture of 3,3-dichloro-1,1,1,2,2-pentafluoropropane and 1,3-dichloro-1,1,2,2,3-pentafluoropropane, and the balance of methanol, with trace amounts of nitromethane. Those having ordinary skill in the art will select the solvent or a mixture of solvents suitable for a particular polymer being dissolved.

The therapeutic substance which can be used in the reservoir layer can include any substance capable of exerting a therapeutic or prophylactic effect for a patient. The therapeutic substance may include small molecule substances, peptides, proteins, oligonucleotides, and the like. The therapeutic substance could be designed, for example, to inhibit the activity of vascular smooth muscle cells. It can be directed at inhibiting abnormal or inappropriate migration and/or proliferation of smooth muscle cells to inhibit restenosis.

Examples of therapeutic substances that can be used include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as ANGIOMAX (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)ethoxy]ethyl-rapamycin, and 40-O-tetrazole-rapamycin.

The coatings and methods of the present invention have been described with reference to a stent, such as a balloon expandable or self-expandable stent. The use of the coating is not limited to stents, however, and the coating can also be used with a variety of other medical devices. Examples of the implantable medical device, that can be used in conjunction with the embodiments of this invention include stent-grafts, grafts (e.g., aortic grafts), artificial heart valves, cerebrospinal fluid shunts, pacemaker electrodes, axius coronary shunts and endocardial leads (e.g., FINELINE and ENDOTAK, available from Guidant Corporation). The underlying structure of the device can be of virtually any design. The device can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention. In some embodiments, the device, e.g., the stent, can be made from the copolymers of the invention.

"MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

3. EXAMPLES

The following examples are provided to further illustrate embodiments of the present invention.

Example 1

A copolymer, co-poly-{N,N'-sebacoyl-bis-(L-leucine)-1,6-hexylene diester}, having formula (VII) can be synthesized and used in practice of the invention:

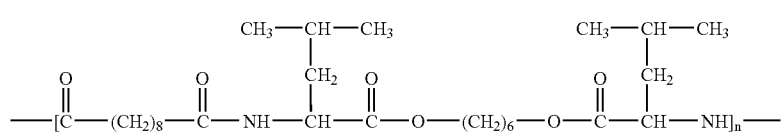

(VII)

wherein n can be between 85 and 95, for example, 90.

To synthesize the copolymer (VII), a diol-diamine substance of a family having formula (III) can be reacted with a dicarboxylic acid substance of a family of having formula (IV).

The diol-diamine substance can be the di-p-toluenesulphonic acid salt of bis-(L-leucine)-1,6-hexylene diester and can be synthesized by condensation of L-leucine with 1,6-hexanediol using a p-toluenesulphonic acid catalyst.

The dicarboxylic acid substance can be the di-p-nitrophenyl derivative of sebacic acid, and can be synthesized by the condensation of p-nitrophenol with sebacoyl chloride. The conditions for the synthesis of the diol-diamine and the dicarboxylic acid substances can be determined by those having ordinary skill in the art.

The synthesis of copolymer (VII) can be carried out according to the following procedure. About 100.3 g (0.15 mole) of the di-p-toluenesulphonic acid salt of bis-(L-leucine)-1,6-hexylene diester can be mixed with about 105 ml dry DMAC and can be reacted with about 66.67 g (0.15 mole) of di-p-nitrophenyl sebacinate. The reagents can be combined in a one liter round bottom flask equipped with a mechanical stirrer, a nitrogen inlet and a heated oil bath, at room temperature.

About 46.2 ml (0.33 mole) of dry triethylamine can be then added to the flask, with stirring, the temperature of the reaction mixture can be increased to about 80° C., and the solution can be stirred for about 10 hours. The viscous reaction mixture can then be cooled to room temperature, diluted with about 250 ml of ethanol, and slowly added to about 2 liters of de-ionized water with stirring. The polymer can then be isolated by filtration, re-suspended in about 1 liter of deionized water, and again isolated by filtration. The process of re-suspension and filtration can then be repeated. Finally, the polymer can be dried at about 30° C. under reduced pressure overnight.

Example 2

A copolymer, co-poly-{N,N'-sebacoyl-bis-(L-leucine)-1,4-butylene diester} having formula (VII) can be synthesized and used in practice of the invention:

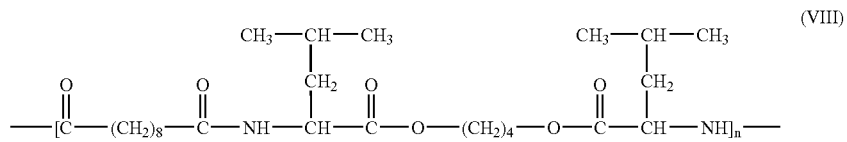

(VIII)

wherein n is between 140 and 160, for example, 150.

The copolymer (VIII) can be synthesized in the same manner as the copolymer (VII) described in Example 1, except the 1,4-butanediol derivative can be used instead of 1,6-hexanediol derivative. Specifically, the following synthetic procedure can be used.

About 99.13 g (0.15 mole) of the di-p-toluenesulphonic acid salt of bis-(L-leucine)-1,4-butylene diester can be mixed with about 105 ml dry DMAC and can be reacted with about 66.67 g (0.15 mole) of di-p-nitrophenyl sebacinate. The reagents can be combined in a one liter round bottom flask equipped with a mechanical stirrer, a nitrogen inlet and a heated oil bath, at room temperature.

About 46.2 ml (0.33 mole) of dry triethylamine can be then added to the flask, with stirring, the temperature of the reaction mixture can be increased to about 80° C., and the solution can be stirred for about 12 hours. The viscous reaction mixture can then be cooled to room temperature, diluted with about 250 ml of ethanol, and slowly added to about 2 liters of de-ionized water with stirring. The polymer can then be isolated by filtration, re-suspended in about 1 liter of deionized water, and again isolated by filtration. The process of re-suspension and filtration can then be repeated. Finally, the polymer can be dried at about 30° C. under reduced pressure overnight.

Example 3

A copolymer, co-poly-{N,N'-adipoyl-bis-(L-leucine)-1,4-butylene diester} having formula (IX) can be synthesized and used in practice of the invention:

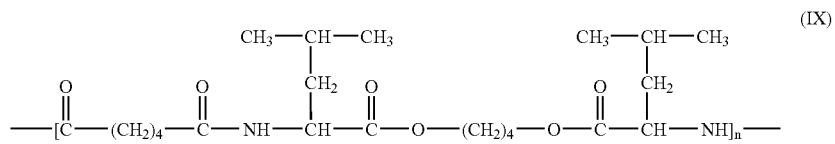

(IX)

wherein n is between 140 and 160, for example, 150.

The copolymer (IX) can be synthesized using in the same manner as the copolymer (VIII) described in Example 2, except adipic acid can be used instead of sebacic acid. Specifically, the following synthetic procedure can be used.

About 99.13 g (0.15 mole) of the di-p-toluenesulphonic acid salt of bis-(L-leucine)-1,4-butylene diester can be mixed with about 76 ml dry DMAC and can be reacted with about 58.2 g (0.15 mole) of di-p-nitrophenyl adipate. The reagents can be combined in a one liter round bottom flask equipped with a mechanical stirrer, a nitrogen inlet and a heated oil bath, at room temperature.

About 46.2 ml (0.33 mole) of dry triethylamine can be then added to the flask, with stirring, the temperature of the reaction mixture can be increased to about 80° C., and the solution can be stirred for about 10 hours. The viscous reaction mixture can then be cooled to room temperature, diluted with about 220 ml of ethanol, and slowly added to about 2 liters of de-ionized water with stirring. The polymer can then be isolated by filtration, re-suspended in about 1 liter of deionized water, and again isolated by filtration. The process of re-suspension and filtration can then be repeated. Finally, the polymer can be dried at about 30° C. under reduced pressure overnight.

Example 4

A copolymer, co-poly-{N,N'-adipoyl-bis-(L-alanine)-1,4-butylene diester}, having formula (X) can be synthesized and used in practice of the invention:

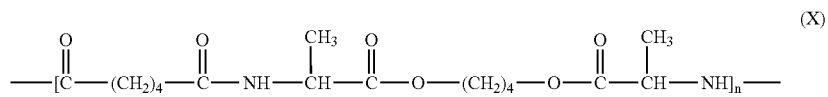

(X)

wherein n is between 250 and 300, for example, 275.

To synthesize copolymer (X), a diol-diamine substance of a family having formula (III) can be reacted with a dicarboxylic acid substance of a family of having formula (IV).

The diol-diamine substance can be the di-p-toluenesulphonic acid salt of bis-(L-alanine)-1,4-butylene diester and can be synthesized by condensation of L-alanine with 1,4-butanediol using a p-toluenesulphonic acid catalyst.

The dicarboxylic acid substance can be the di-p-nitrophenyl derivative of adipic acid, and can be synthesized by the condensation of p-nitrophenol with adipoyl chloride. The conditions for the synthesis of the diol-diamine and the dicarboxylic acid substances can be determined by those having ordinary skill in the art.

The synthesis of copolymer (X) can be carried out according to the following procedure. About 86.4 g (0.15 mole) of the di-p-toluenesulphonic acid salt of bis-(L-alanine)-1,4-butylene diester can be mixed with about 72 ml dry DMAC and can be reacted with about 58.2 g (0.15 mole) of di-p-nitrophenyl adipate. The reagents can be combined in a one liter round bottom flask equipped with a mechanical stirrer, a nitrogen inlet and a heated oil bath, at room temperature.

About 46.2 ml (0.33 mole) of dry triethylamine can be then added to the flask, with stirring, the temperature of the reaction mixture can be increased to about 80° C., and the solution can be stirred for about 16 hours. The viscous reaction mixture can then be cooled to room temperature, diluted with about 205 ml of ethanol, and slowly added to about 2 liters of de-ionized water with stirring. The polymer can then be isolated by filtration, re-suspended in about 1 liter of deionized water, and again isolated by filtration. The process of re-suspension and filtration can then be repeated. Finally, the polymer can be dried at about 30° C. under reduced pressure overnight.

Example 5

A first composition can be prepared by mixing the following components:

(a) about 2.0 mass % co-poly-{N,N'-sebacoyl-bis-(L-leucine)-1,4-butylene diester}, the copolymer having formula (VIII); and (b) the balance, absolute (100%) ethanol.

The first composition can be applied onto the surface of bare 12 mm small VISION stent (available from Guidant Corporation). The coating can be sprayed and dried to form a primer layer. A spray coater can be used having a 0.014 round nozzle maintained at ambient temperature with a feed pressure 2.5 psi (0.17 atm) and an atomization pressure of about 15 psi (1.02 atm). About 20 μg of the coating can be applied in one spray pass. Between the spray passes the stent can be dried for about 10 seconds in a flowing air stream at about 50° C. About 110 µg of wet coating can be applied. The stents can be baked at about 50° C. for about one hour, yielding a primer layer composed of approximately 100 µg of copolymer (VII).

A second composition can be prepared by mixing the following components:
(a) about 2.0 mass % copolymer of formula (VIII);
(b) about 2.0 mass % EVEROLIMUS; and
(c) the balance, absolute ethanol.

The second composition can be applied onto the dried primer layer, using the same spraying technique and equipment used for applying the primer layer, to form the drug-polymer layer. About 120 µg of wet coating can be applied followed by drying and baking at about 50° C. for about 1 hour, yielding a dry drug-polymer layer having solids content of about 110 µg.

A third composition can be prepared by mixing the following components:
(a) about 2.0 mass % copolymer of formula (VIII); and
(b) the balance, absolute ethanol.

The third composition can be applied onto the dried drug-polymer layers, using the same spraying technique and equipment used for applying the primer and drug-polymer layers, to form a topcoat layer. About 220 µg of wet coating can be applied followed by drying and baking at about 50° C. for about 1 hour, yielding a dry topcoat layer having solids content of about 200 µg.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A medical article comprising an implantable substrate having a coating, the coating including a polymeric product of a reaction between a diol-diamine and a dicarboxylic acid, wherein the diol-diamine comprises a unit derived from a diol and
wherein the polymeric product comprises a copolymer of a formula

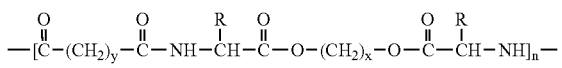

wherein:
R is selected from a group consisting of hydrogen, methyl, iso-propyl, sec-butyl, iso-butyl, benzyl, methyl mercaptoethyl, methylene amide, and ethylene amide;
x is an integer having a value between 2 and 16;
y is an integer having a value between 0 and 16; and
n is an integer having a value between 35 and 1,100.

2. The medical article of claim 1, wherein the implantable substrate is a stent.

3. The medical article of claim 1, wherein the diol-diamine is a product of condensation of two molecules of an amino acid or a mixture of two amino acids and one molecule of the diol.

4. The medical article of claim 3, wherein the amino acid comprises a substance having the formula $H_2N-CHR-COOH$, wherein R is selected from a group consisting of hydrogen, methyl, iso-propyl, sec-butyl, iso-butyl, benzyl, methyl mercaptoethyl, methylene amide, and ethylene amide.

5. The medical article of claim 3, wherein the amino acid is selected from a group consisting of glycine, alanine, valine, isoleucine, leucine, phenyl alanine, methionine, asparagine, glutamine, proline, and mixtures thereof.

6. The medical article of claim 1, wherein the diol comprises a substance having the formula $HO-(CH_2)_x-OH$, wherein x is an integer having a value between 2 and 16.

7. The medical article of claim 1, wherein the diol is selected from a group consisting of ethylene glycol, 1,2-propanediol, 1,3-propanediol, 1,4-butane diol, 1,5-pentanediol, 1,6-hexanediol, 1,7-heptanediol, 1,8-octanediol, 1,9-nonanediol, 1,10-decanediol, 1,11-undecanediol, and 1,12-dodecanediol, and mixtures thereof.

8. The medical article of claim 1, wherein the dicarboxylic acid comprises a substance having the formula $HOOC-(CH_2)_y-COOH$, wherein y is an integer having a value between 0 and 16.

9. The medical article of claim 1, wherein the dicarboxylic acid is selected from a group consisting of oxalic acid, malonic acid, succinic acid, glutaric acid, adipic acid, pimelic acid, suberic acid, azelaic acid, sebacic acid, undecanedioic acid, dodecanedioic acid, brassylic acid, tetradecanedioic acid, pentadecanedioic acid, thapsic acid, and mixtures thereof.

10. A medical article comprising an implantable substrate having a coating, the coating including a copolymer having a formula

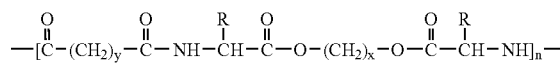

wherein:
R is selected from a group consisting of hydrogen, methyl, iso-propyl, sec-butyl, iso-butyl, benzyl, methyl mercaptoethyl, methylene amide, and ethylene amide;
x is an integer having a value between 2 and 16;
y is an integer having a value between 0 and 16; and
n is an integer having a value between 35 and 1,100.

11. A medical article comprising an implantable substrate having a coating, the coating including a copolymer having a formula

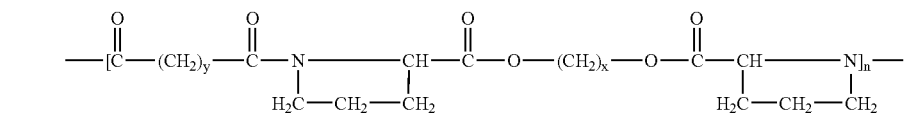

wherein x is an integer having a value between 2 and 16; y is an integer having a value
between 0 and 16; and n is an integer having a value between 35 and 1,100.

12. A method for fabricating a medical article, the method including:
(a) synthesizing a copolymer; and
(b) forming a coating comprising the copolymer on at least a portion of an implantable substrate, the synthesizing of the copolymer including reacting a diol-diamine with a dicarboxylic acid,

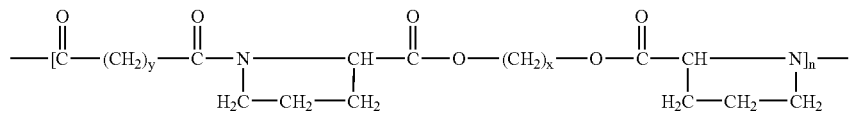

wherein the diol-diamine comprises a unit derived from a diol.

13. The method of claim 12, wherein the implantable substrate is a stent.

14. The method of claim 12, wherein the diol-diamine is a product of condensation of two molecules of an amino acid or a mixture of two amino acids and one molecule of the diol.

15. The method of claim 14, wherein the amino acid comprises a substance having the formula $H_2N-CHR-COOH$, wherein R is selected from a group consisting of hydrogen, methyl, iso-propyl, sec-butyl, iso-butyl, benzyl, methyl mercaptoethyl, methylene amide, and ethylene amide.

16. The method of claim 14, wherein the amino acid is selected from a group consisting of glycine, alanine, valine, isoleucine, leucine, phenyl alanine, methionine, asparagine, glutamine, proline, and mixtures thereof.

17. The method of claim 12, wherein the diol comprises a substance having the formula $HO-(CH_2)_x-OH$, wherein x is an integer having a value between 2 and 16.

18. The method of claim 12, wherein the dicarboxylic acid comprises a substance having the formula $HOOC-(CH_2)_y-COOH$, wherein y is an integer having a value between 0 and 16.

19. The method of claim 12, wherein the dicarboxylic acid is selected from a group consisting of oxalic acid, malonic acid, succinic acid, glutaric acid, adipic acid, pimelic acid, suberic acid, azelaic acid, sebacic acid, undecanedioic acid, dodecanedioic acid, brassylic acid, tetradecanedioic acid, pentadecanedioic acid, thapsic acid, and mixtures thereof.

20. A method for fabricating a medical article, the method including:
(a) synthesizing a copolymer; and
(b) forming a coating comprising the copolymer on at least a portion of an implantable substrate, wherein the copolymer has a formula

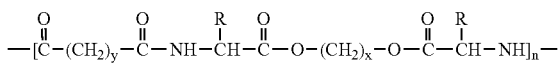

wherein:
R is selected from a group consisting of hydrogen, methyl, iso-propyl, sec-butyl, iso-butyl, benzyl, methyl mercaptoethyl, methylene amide, and ethylene amide;
x is an integer having a value between 2 and 16;
y is an integer having a value between 0 and 16; and
n is an integer having a value between 35 and 1,100.

21. The method of claim 20, wherein the implantable substrate is a stent.

22. A method for fabricating a medical article, the method including:
(a) synthesizing a copolymer; and
(b) forming a coating comprising the copolymer on at least a portion of an implantable substrate, wherein the copolymer has a formula

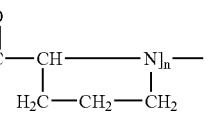

wherein x is an integer having a value between 2 and 16; y is an integer having a value between 0 and 16; and n is an integer having a value between 35 and 1,100.

23. The medical article of claim 10, wherein the implantable substrate is a stent.

24. The method of claim 12, wherein the diol is selected from a group consisting of ethylene glycol, 1,2-propanediol, 1,3-propanediol, 1,4-butane diol, 1,5-pentanediol, 1,6-hexanediol, 1,7-heptanediol, 1,8-octanediol, 1,9-nonanediol, 1,10-decanediol, 1,11-undecanediol, and 1,12-dodecanediol, and mixtures thereof.

25. A method for fabricating a medical article, the method including:
forming a coating comprising a copolymer on at least a portion of an implantable substrate, the copolymer being a product of a reaction between a diol-diamine and a dicarboxylic acid,
wherein the diol-diamine comprises a unit derived from a diol and
wherein the polymeric product comprises a copolymer of a formula

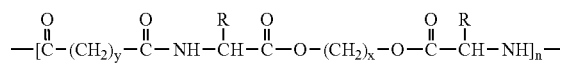

wherein:
R is selected from a group consisting of hydrogen, methyl, iso-propyl, sec-butyl, iso-butyl, benzyl, methyl mercaptoethyl, methylene amide, and ethylene amide;
x is an integer having a value between 2 and 16;
y is an integer having a value between 0 and 16; and
n is an integer having a value between 35 and 1,100.

26. A method for fabricating a medical article, the method including:
forming a coating comprising a copolymer on at least a portion of an implantable substrate, wherein the copolymer has a formula

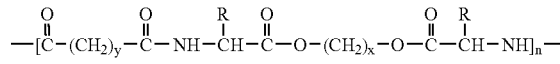

wherein:
R is selected from a group consisting of hydrogen, methyl, iso-propyl, sec-butyl, iso-butyl, benzyl, methyl mercaptoethyl, methylene amide, and ethylene amide;
x is an integer having a value between 2 and 16;
y is an integer having a value between 0 and 16; and
n is an integer having a value between 35 and 1,100.

27. A method for fabricating a medical article, the method including:
forming a coating comprising a copolymer on at least a portion of an implantable substrate, wherein the copolymer has a formula
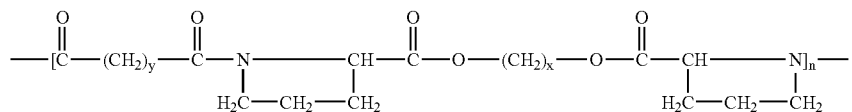
wherein x is an integer having a value between 2 and 16; y is an integer having a value between 0 and 16; and n is an integer having a value between 35 and 1,100.
* * * * *